US009164014B2

(12) United States Patent
Ito

(10) Patent No.: US 9,164,014 B2
(45) Date of Patent: Oct. 20, 2015

(54) THIN SECTION FABRICATION APPARATUS AND METHOD OF FABRICATING THIN SECTION

(71) Applicant: SAKURA FINETEK JAPAN CO., LTD., Tokyo (JP)

(72) Inventor: Tetsumasa Ito, Kawasaki (JP)

(73) Assignee: SAKURA FINETEK JAPAN CO., LTD., Tokyo (JP)

( * ) Notice: Subject to any disclaimer, the term of this patent is extended or adjusted under 35 U.S.C. 154(b) by 0 days.

(21) Appl. No.: 14/376,552

(22) PCT Filed: Feb. 5, 2013

(86) PCT No.: PCT/JP2013/052554
§ 371 (c)(1),
(2) Date: Aug. 4, 2014

(87) PCT Pub. No.: WO2013/118699
PCT Pub. Date: Aug. 15, 2013

(65) Prior Publication Data
US 2015/0017679 A1  Jan. 15, 2015

(30) Foreign Application Priority Data

Feb. 8, 2012  (JP) .................................. 2012-025281

(51) Int. Cl.
*A61B 10/00*  (2006.01)
*G01N 1/31*  (2006.01)
*G01N 1/06*  (2006.01)

(52) U.S. Cl.
CPC .. *G01N 1/31* (2013.01); *G01N 1/06* (2013.01); *G01N 2001/068* (2013.01)

(58) Field of Classification Search
CPC .................................. G01N 1/31; G01N 1/06
See application file for complete search history.

(56) References Cited

U.S. PATENT DOCUMENTS 8,074,547 B2   12/2011   Ito et al.

FOREIGN PATENT DOCUMENTS

| JP | 2007-212276 | 8/2007 |
| JP | 2007-212387 | 8/2007 |
| JP | 2008-020293 | 1/2008 |
| JP | 2010-044069 | 2/2010 |
| JP | 4784936 | 7/2011 |
| WO | 2012/147730 | 11/2012 |

OTHER PUBLICATIONS

International Search Report from corresponding PCT Application No. PCT/JP2013/052554 dated Mar. 19, 2013. English translation attached.

*Primary Examiner* — Jyoti Nagpaul
(74) *Attorney, Agent, or Firm* — Grossman, Tucker, Perreault & Pfleger, PLLC

(57) ABSTRACT

A thin section fabrication apparatus includes an epi-imaging data acquisition unit that performs imaging by radiating epi-illumination and acquires imaging data, a diffusion imaging data acquisition unit that performs imaging by radiating diffusion illumination and acquires imaging data, an exposed shape extraction unit that extracts an exposed shape of an exposure portion of the biological sample which is exposed to a surface of the embedding block, based on the imaging data acquired by the epi-imaging data acquisition unit, an embedded shape extraction unit that extracts an embedded shape of an embedding portion of the biological sample which is embedded in the embedding block, based on the imaging data acquired by the diffusion imaging data acquisition unit, and a control unit that determines ending of the preliminary cutting by comparing the exposed shape extracted by the exposed shape extraction unit and the embedded shape extracted by the embedded shape extraction unit.

7 Claims, 9 Drawing Sheets

THIN SECTION FABRICATION APPARATUS AND METHOD OF FABRICATING THIN SECTION

TECHNICAL FIELD

The present invention relates to a thin section fabrication apparatus and a method of fabricating a thin section.

Priority is claimed on Japanese Patent Application No. 2012-025281, filed Feb. 8, 2012, the content of which is incorporated herein by reference.

BACKGROUND ART

When pathological examinations are performed on tissue or the like of humans or animals suffering from disease, generally, after the tissue is sliced into sections with a thickness of 2 to 5 μm and is subjected to various dyeing methods, a microscopic observation is performed to examine the tissue.

At this time, a diagnosis is performed based on information acquired in the past. Particularly, pathology is composed based on a large amount of information with respect to a disease and a form change of the tissue. Accordingly, in order to effectively use the information acquired in the past, it is necessary to cut a sample, which is a test object, along a specific cross-section, and to slice the sample so that tissue required for the diagnosis appears on the surface of the sample.

In general, in order to slice soft tissue and cells so as not to break forms of the tissue and the cells, the sample is embedded in paraffin in advance, and an embedding block is fabricated. Moreover, the embedding block is thinly sliced (is thinly sectioned) to a thickness of 2 to 5 m, and thus, a thin section is fabricated. Accordingly, even when the test object is soft tissues or the like, the soft tissue can be very thinly sliced without destroying the form of the tissue. The thin section is fixed onto a substrate such as a glass slide, and the thin-section sample is fabricated. Generally, an operator performs the microscopic observation on the thin section sample, and performs the above-described pathological examination.

When the thin section is fabricated, two processes such as a preliminary cutting process (rough cutting process) and a main cutting process are performed, and thus, the thin section is cut out from the embedding block. In the preliminary cutting, the embedding block is gradually sliced so that the surface is flattened, and the surface of the sample embedded in the paraffin is exposed. Moreover, in the main cutting, the thin section is cut out to have a predetermined thickness with respect to the surface of the embedding block in which the sample is securely exposed.

Particularly, from the viewpoint of the above-described pathology, it is preferable that in the fabricated thin section, the sample be maintained in a desired exposure state which is suitable for the observation. Therefore, the preliminary cutting is important, and thus, it is necessary to carefully perform the preliminary cutting.

However, since the paraffin embedded with the sample becomes clouded due to crystallization at the time of solidification, after the embedding block is fabricated, it is impossible to confirm in advance from the external view of the embedding block that what form the sample has when embedded in the paraffin. Therefore, when the preliminary cutting is performed, it is necessary that the operator appropriately adjusts a cutting amount of a cutting blade, an angle of a support frame on which the embedding block is placed, or the like while always observing the surface of the sample exposed from the paraffin, and performs adjustment so that a biological sample has a desired exposure state. Restarting of the operation is not possible, and the cutting should be performed dozens of times or more until a desired surface is exposed.

Therefore, skill and attentiveness for a long period of time are required, and there is a large burden on the operator.

A thin section fabrication apparatus is suggested which effectively performs preliminary cutting on an embedding block so that a biological sample in the embedding block is securely maintained at a desired exposure state (for example, refer to Patent Document 1).

In the thin section fabrication apparatus disclosed in Patent Document 1, an epi-illumination system that radiates epi-illumination light to the embedding block, a diffusion illumination system that radiates diffusion illumination light to the embedding block, and an imaging unit that images the embedding block under the epi-illumination light and the diffusion illumination light are provided, a state in which imaging data of the embedding block imaged under the epi-illumination light and imaging data of the embedding block imaged under the diffusion illumination light overlap each other is displayed on a monitor, and thus, an operator can easily set a cutting amount, an inclination angle, or the like of the embedding block at the time of the preliminary cutting while confirming with the display of the monitor.

When the epi-illumination light is radiated to the embedding block, a luminance difference is generated between a portion of an embedding agent such as the paraffin and the exposed portion of the biological sample. On the other hand, when the diffusion illumination light is radiated to the embedding block, the light enters the inner portion of the embedding block, abuts the biological sample which is not exposed to a cutting surface, and is reflected.

In the thin section fabrication apparatus disclosed in Patent Document 1, by focusing attention on the above-described characteristics, the imaging data obtained under the epi-illumination light and the imaging data obtained under the diffusion illumination light are overlapped with each other and displayed on the monitor. Accordingly, the operator can accurately understand the state of the surface of the embedding block and the state of the biological sample in the embedding block.

PRIOR ART DOCUMENTS

Patent Documents

[Patent Document 1] Japanese Patent No. 4784936

DISCLOSURE OF INVENTION

Problems to be Solved by the Invention

In the thin section fabrication apparatus of the related art, the imaging data obtained under the epi-illumination light and the imaging data obtained under the diffusion illumination light are overlapped with each other and displayed on the monitor, and thus, the operator is able to understand the surface state and the inner state of the embedding block. After this, however, with respect to determination of whether or not the biological sample has a desired exposure state, and instruction of a cutting amount or the like in order to get close to the desired exposure state, the operator should perform the determination, the instruction, or the like each time while relying on the operator's intuition.

The present invention provides a thin section fabrication apparatus and a method of fabricating the thin section, which enable the biological sample in the embedding block to reach a desired exposure state automatically and securely in a preliminary cutting step.

Means for Solving the Problems

According to a first aspect of the present invention, a thin section fabrication apparatus is provided, including: an epi-imaging data acquisition unit that radiates epi-illumination, performs imaging on a surface of an embedding block in which a biological sample is embedded, and acquires imaging data; a diffusion imaging data acquisition unit that radiates diffusion illumination, performs imaging on the surface of the embedding block, and acquires imaging data; an exposed shape extraction unit that extracts an exposed shape of an exposure portion of the biological sample which is exposed to a surface of the embedding block, based on the imaging data acquired by the epi-imaging data acquisition unit; an embedded shape extraction unit that extracts an embedded shape of an embedding portion of the biological sample which is embedded in the embedding block, based on the imaging data acquired by the diffusion imaging data acquisition unit; and a control unit that determines an ending of the preliminary cutting by comparing the exposed shape extracted by the exposed shape extraction unit and the embedded shape extracted by the embedded shape extraction unit, and controls an operation of the preliminary cutting.

In this case, when the exposed shape of the biological sample satisfies a predetermined condition with respect to the embedded shape, it is possible to determine that the biological sample is in a desired exposure state. Moreover, the control unit determines the ending of the preliminary cutting by comparing the exposed shape and the embedded shape, and thus, in the biological sample in the embedding block, the desired exposure state can be automatically and securely obtained.

According to a second aspect of the present invention, in the thin section fabrication apparatus of the first aspect, the exposed shape extraction unit may obtain an exposed area of the biological sample which is exposed to the surface of the embedding block, as the exposed shape, the embedded shape extraction unit may obtain a projected area of the biological sample which is embedded in the embedding block, as the embedded shape, and the control unit may end the preliminary cutting when a ratio between the exposed area obtained by the exposed shape extraction unit and the projected area obtained by the embedded shape extraction unit is larger than a first predetermined value.

In this case, when the ratio between the exposed area and the projected area of the biological sample is larger than the first predetermined value, the exposed area is close to the projected area which is a maximum value, and thus, it is possible to determine that the biological sample is in the desired exposure state. At this time, the control unit ends the preliminary cutting, and thus, in the biological sample in the embedding block, the desired exposure state can be automatically and securely obtained.

According to a third aspect of the present invention, the thin section fabrication apparatus of the first or second aspect may further include a vector calculation unit that obtains a center of the exposure portion of the biological sample based on the imaging data acquired by the epi-imaging data acquisition unit, obtains a center of the embedding portion of the biological sample based on the imaging data acquired by the diffusion imaging data acquisition unit, and calculates a direction and a magnitude of a vector from the center of the exposure portion toward the center of the embedding portion, and when the magnitude of the vector calculated by the vector calculation unit is larger than a second predetermined value, the control unit may control a relative posture between the embedding block and the cutting blade based on the direction of the vector so that the vector is decreased and may perform the preliminary cutting.

In this case, when the magnitude of the vector from the center of the exposure portion toward the center of the embedding portion is increased, the exposure portion exists at a position separated from the center of the embedding portion, and thus, it is considered that the biological sample is embedded in the embedding block in a state where the sample is largely inclined. In this state, even when the preliminary cutting proceeds, the biological sample is not largely exposed. On the other hand, when the magnitude of the vector is decreased, the exposure portion exists at a position close to the center of the embedding portion, and thus, it is considered that the biological sample is embedded in a state where the sample has little inclination. In this state, if the preliminary cutting is performed, the biological sample is largely exposed, and thus, a desired exposure state can be obtained. Accordingly, when the vector is larger than the second predetermined value, the preliminary cutting is performed so that the vector is decreased by the control unit, and thus, in the biological sample in the embedding block, the desired exposure state can be automatically and securely obtained. Moreover, the relative posture between the embedding block and a cutting blade is controlled based on the direction of the vector, and thus, the magnitude of the vector can be rapidly and securely decreased.

In addition, "the center of the exposure portion" may be the gravity center position of the exposure portion of the biological sample and may be the center of the maximum width portion of the exposure portion. Similarly, "the center of the embedding portion" may be the gravity center position of the embedding portion of the biological sample, and may be the center of the maximum width portion of the embedding portion.

According to a fourth aspect of the present invention, in the thin section fabrication apparatus of any one of the first to third aspects, the control unit may perform the preliminary cutting so that a cutting amount of the preliminary cutting is decreased as the exposed shape extracted by the exposed shape extraction unit approaches the embedded shape extracted by the embedded shape extraction unit.

In this case, in the preliminary cutting process of the embedding block, when the exposure portion of the biological sample on the embedding block is largely separated from the desired region of the embedding portion of the biological sample, the embedding block can be effectively cut by increasing a one-time cutting amount of the preliminary cutting. In addition, if the exposure portion of the biological sample on the embedding block approaches the desired region of the embedding portion of the biological sample, the one-time cutting amount of the preliminary cutting is decreased, and thus, the desired exposure state can be securely obtained in the biological sample without passing through the desired exposure state. Moreover, the surface of the embedding block can be further smoothened.

According to a fifth aspect of the present invention, the thin section fabrication apparatus of any one of the first to fourth aspects may further include a cutting blade that performs the preliminary cutting on the surface of the embedding block and causes the biological sample to be in a desired exposure state.

According to a sixth aspect of the present invention, a method of fabricating a thin section is provided, in which after preliminary cutting is performed on a surface of an embedding block, in which a biological sample is embedded, by a cutting blade so as to cause the biological sample to be in a desired exposure state, main cutting is performed on the embedding block to cut out a thin section, including: an epi-imaging data acquisition process of performing imaging on the surface of the embedding block by radiating epi-illumination to acquire imaging data; a diffusion imaging data acquisition process of performing imaging on the surface of the embedding block by radiating diffusion illumination to acquire imaging data; an exposed shape extraction process of extracting an exposed shape of an exposure portion of the biological sample which is exposed to a surface of the embedding block, based on the imaging data acquired in the epi-imaging data acquisition process; an embedded shape extraction process of extracting an embedded shape of an embedding portion of the biological sample which is embedded in the embedding block, based on the imaging data acquired in the diffusion imaging data acquisition process; a preliminary cutting performance process of performing the preliminary cutting on the surface of the embedding block by a cutting blade; and a preliminary cutting ending determination process of determining the ending of the preliminary cutting by comparing the exposed shape extracted in the exposed shape extraction process and the embedded shape extracted in the embedded shape extraction process.

Effects of the Invention

According to the aspects of the present invention, an exposed shape and an embedded shape of a biological sample in an embedding block are extracted based on imaging data acquired by the epi-imaging data acquisition unit and the diffusion imaging data acquisition unit, and an ending of preliminary cutting is determined by comparing the extracted exposed shape and the embedded shape. Therefore, in the biological sample in the embedding block, a desired exposure state can be automatically and securely obtained in the preliminary cutting stage.

EMBODIMENTS FOR CARRYING OUT THE INVENTION

Hereinafter, an embodiment of the present invention is described with reference to the drawings.

Figure 1:
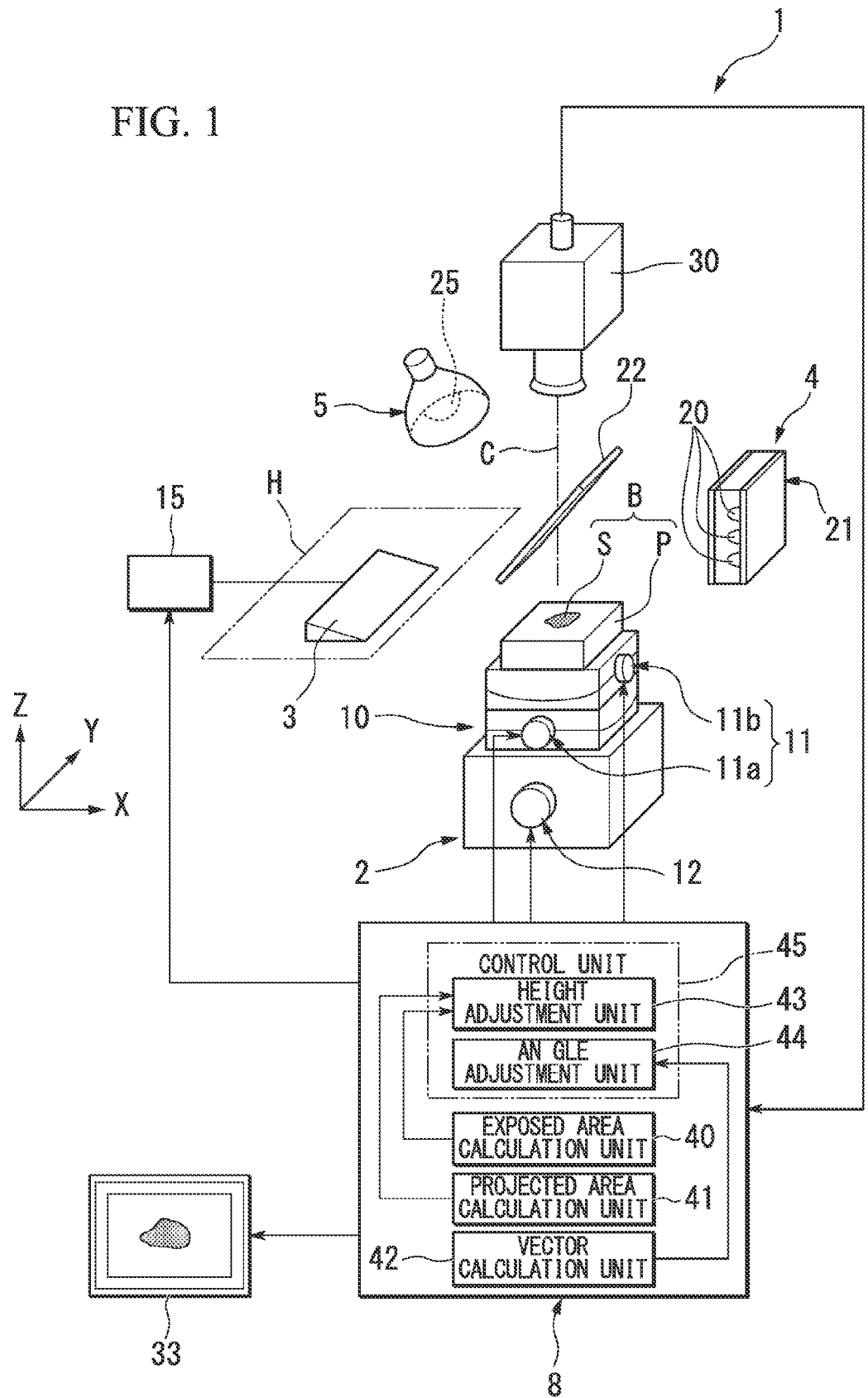
FIG. 1 is a schematic structure diagram showing a thin section fabrication apparatus according to an embodiment of the present invention.

As shown in FIG. 1, a thin section fabrication apparatus 1 is an apparatus which fabricates a thin section by performing a main cutting on an embedding block B after a preliminary cutting is performed on the embedding block B in which a biological sample S is embedded in a paraffin (embedding agent) P. In addition, for example, the biological sample S is tissue such as that isolated from an internal organ or the like removed from a human body, experimental animal, or the like, and is tissue which is appropriately selected in a medical field, a pharmaceutical field, a food field, a biological field, or the like.

As shown in FIG. 1, the thin section fabrication apparatus 1 of the present embodiment includes a frame portion 2 to which the embedding block B is fixed, a cutting blade 3 which moves along one virtual plane H, an epi-illumination system 4 which radiates epi-illumination light to the embedding block B, a diffusion illumination system 5 which radiates diffusion illumination light to the embedding block B, an imaging unit 30 which images the embedding block B on the frame portion 2 under illumination light by the epi-illumination system 4 or the diffusion illumination system 5, a monitor 33 which displays an image imaged by the imaging unit 30 and a processed image in which processing is applied to the imaged image, and a general control unit 8 which generally controls the above-described component members.

The frame portion 2 includes a support frame 10 on which the embedding block B is placed, a rotation mechanism 11 which rotates the support frame 10 around two axes of an X axis and a Y axis orthogonal to each other on the one virtual plane H, and a moving mechanism 12 which moves the support frame 10 in a Z axis direction orthogonal to the one virtual plane H. Moreover, the frame portion 2 is disposed on an optical axis C of the epi-illumination system 4.

The rotation mechanism 11 includes a Y axis rotation mechanism 11a which rotates the support frame 10 around the Y axis and an X axis rotation mechanism 11b which rotates the support frame 10 around the X axis, and is operated based on instruction from the general control unit 8.

The moving mechanism 12 moves the rotation mechanism 11 and the support frame 10 in the Z axis direction, and similar to the rotation mechanism 11, is operated based on the instruction from the general control unit 8.

The cutting blade 3 is connected to a cutting blade-moving mechanism 15 which moves in the X axis direction, and moves along the one virtual plane H. The cutting blade-moving mechanism 15 receives the instruction from the general control unit 8 and is operated, and accordingly, a movement speed (cutting speed), a cutting timing, or the like of the cutting blade 3 is controlled.

In addition, the general control unit 8 has a control unit 45 which includes a height adjustment unit 43 which controls the moving mechanism 12 of the frame portion 2, and an angle adjustment unit 44 which controls the rotation mechanism 11 of the frame portion 2.

The control unit 45 controls the height adjustment unit 43 so that a large specific region of a cross-section of the biological sample S is exposed to a surface of the embedding block B in a preliminary cutting process of the embedding block B. The moving mechanism 12 appropriately lifts the embedding block B by the height adjustment unit 43, and thus, a cutting amount is adjusted. In addition, the control unit 45 controls the cutting blade-moving mechanism 15, and thus, cutting of the embedding block B is performed by the cutting blade 3.

The epi-illumination system 4 includes an optical axis C which is orthogonal to the one virtual plane H and is directed to the surface (cutting surface) of the embedding block B on the support frame 10. The epi-illumination system 4 includes a surface light source 21 in which a plurality of LEDs 20 are disposed according to a surface shape, an optical system (not shown) which causes light radiated from the surface light source 21 to be parallel light, and a half mirror 22 which reflects the parallel light to be directed to the surface of the embedding block B on the support frame 10 and transmits the reflected light from the embedding block B. Moreover, as the light source, instead of the surface light source 21, a configuration in which light from a point light source passes through a pin hole and a collimating lens to be a parallel light may be used. Moreover, in the present embodiment, the light radiated from the light source (surface light source 21) is reflected by the half mirror 22, and thus, the optical axis C directed to the surface of the embedding block B is obtained. However, without providing the half mirror 22, the light source is disposed to directly oppose the surface of the embedding block B, and thus, the optical axis C may be also obtained.

In addition, the diffusion illumination system 5 includes a light source 25 which radiates the diffusion illumination light.

The imaging unit 30 includes an imaging element which is not shown, and an imaging axis is set to coincide with the optical axis C. Moreover, the imaging unit 30 images the embedding block B from the vertical upper portion of the block under the illumination light of the epi-illumination system 4 and under the illumination light of the diffusion illumination system 5. Each imaging data imaged by the imaging unit 30 is once stored in an image storage unit which is not shown, and is output to the general control unit 8 described below.

Moreover, hereinafter, the imaging data of the embedding block B imaged under the illumination light of the epi-illumination system 4 is referred to as epi-imaging data, and the imaging data of the embedding block B imaged under the illumination light of the diffusion illumination system 5 is referred to as diffusion imaging data.

Moreover, in the present embodiment, the epi-illumination system 4 and the imaging unit 30 configure an epi-imaging data acquisition unit, and the diffusion illumination system 5 and the imaging unit 30 configure a diffusion imaging data acquisition unit.

Figure 2A:
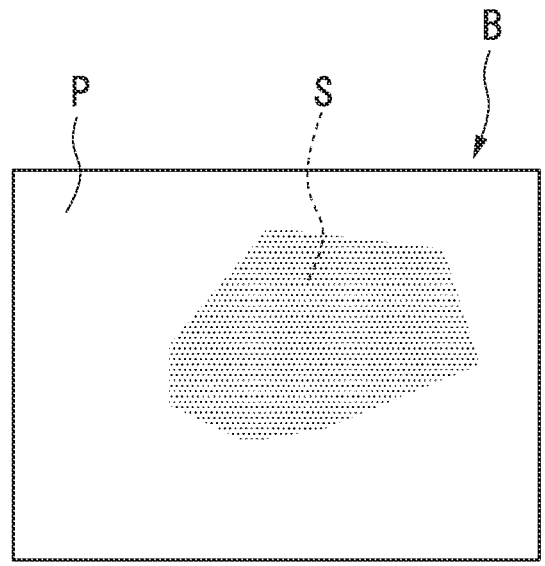
FIG. 2A is a diagram showing imaging data when an embedding block is imaged under diffusion illumination light.
Figure 2B:
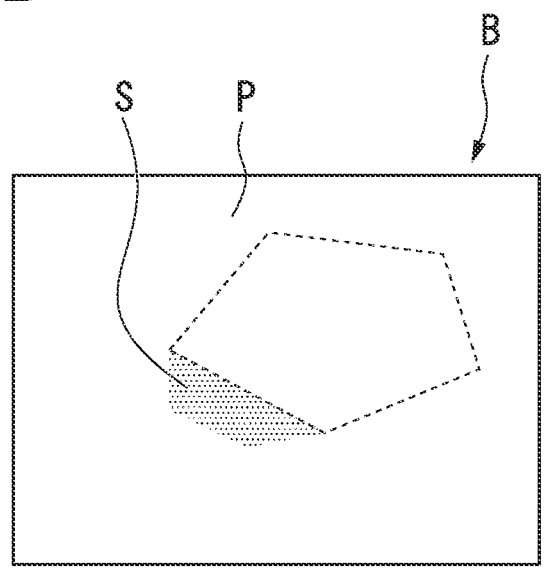
FIG. 2B is a diagram showing imaging data when the embedding block is imaged under epi-illumination light.

FIG. 2A shows the imaging data of the embedding block B under the diffusion illumination light immediately after the preliminary cutting of the embedding block B starts in a state where the rotation mechanism 11 of the frame portion 2 is set to an initial angle, and FIG. 2B shows the imaging data of the embedding block B under the epi-illumination light.

As shown in FIG. 2A, the diffusion illumination light enters the inner portion of the embedding block B, abuts the biological sample S portion which is not exposed to the surface of the embedding block B, and is reflected. Therefore, luminance of the entire projection portion in the optical axis C direction of the biological sample S is different from that of the peripheral portion of the biological sample S.

On the other hand, the epi-illumination light is mirror-reflected at the portion in which the paraffin P exists. However, the epi-illumination light is scattered in the biological sample S portion. Therefore, as shown in FIG. 2B, when the biological sample S is exposed to the surface (cutting surface) of the embedding block B, a difference is generated between intensity of the reflected light in the portion of the biological sample S and intensity of the reflected light in the portion of the paraffin P. That is, the luminance in the exposed portion of the embedding block B is different from the luminance in the peripheral portion thereof.

The general control unit 8 includes an exposed area calculation unit 40 (exposed shape extraction unit) which calculates an exposed area S1 (exposed shape; refer to FIG. 5) of the biological sample S exposed from the surface of the embedding block B in the optical axis C direction based on the epi-imaging data input from the imaging unit 30, a projected area calculation unit 41 (embedded shape extraction unit) which calculates a projected area S0 (embedded shape; refer to FIG. 5) in the optical axis C direction of the biological sample S embedded in the embedding block B based on the diffusion imaging data input from the imaging unit 30, and a vector calculation unit 42 (vector calculation unit) which calculates a direction and a magnitude of a vector V from a center G1 (for example, a gravity center position) of the exposed area S1 portion (exposure portion) of the biological sample S toward a center G0 (for example, a gravity center position) of the projected area S0 portion (embedding portion) of the biological sample S based on the epi-imaging data and the diffusion imaging data input from the imaging unit 30.

Moreover, each of the centers G1 and G0 is not limited to each of the gravity center positions of the exposed area S1 portion (exposure portion) and the projected area S0 portion (embedding portion), and may be a point at which a center line of a maximum width portion in the X direction of the exposed area S1 portion and the projected area S0 portion and a center line of a maximum width portion in the Y direction cross each other.

In the exposed area calculation unit 40, the projected area calculation unit 41, and the vector calculation unit 42 of the general control unit 8, based on the epi-imaging data and the diffusion imaging data input from the imaging unit 30, the outline of the exposure portion and the outline of the embedding portion in the biological sample S are obtained.

Figure 3:
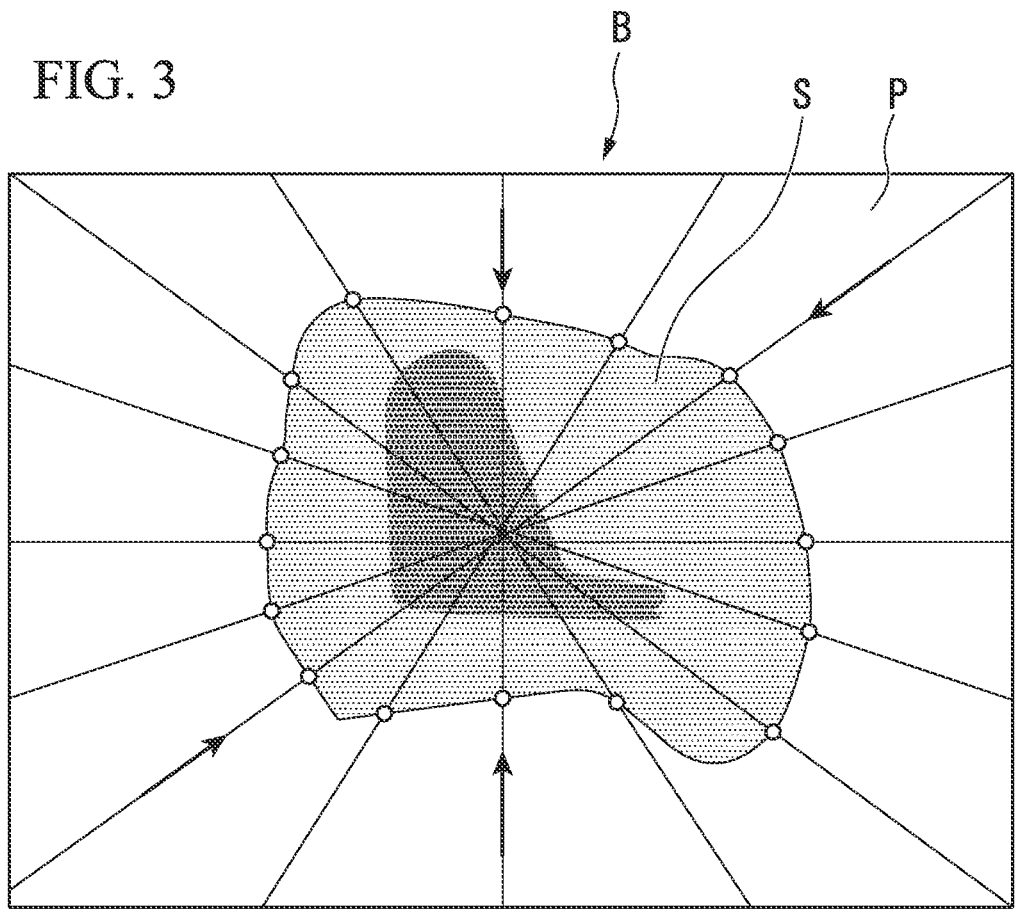
FIG. 3 is a diagram illustrating outline extraction from the imaging data.

FIG. 3 is the imaging data of the embedding block B showing an example of a method of obtaining the outlines of the exposure portion and the embedding portion of the biological sample S.

When an existing region of the biological sample S is extracted from the imaging data, the existing region of the biological sample S can be extracted by binarization of luminance. Alternatively, as shown by arrows in FIG. 3, luminance is differentiated from the outer side of the image toward the center, a point at which the differential value initially exceeds a threshold value is detected as an edge, and the outline of the biological sample S can be effectively extracted by connecting the edges. Moreover, when the outline of the object is extracted in this way, smoothing (blurring processing) of the image may be performed as preprocessing if necessary. When the smoothing is performed, noise due to the differentiation can be decreased.

Figure 4A:
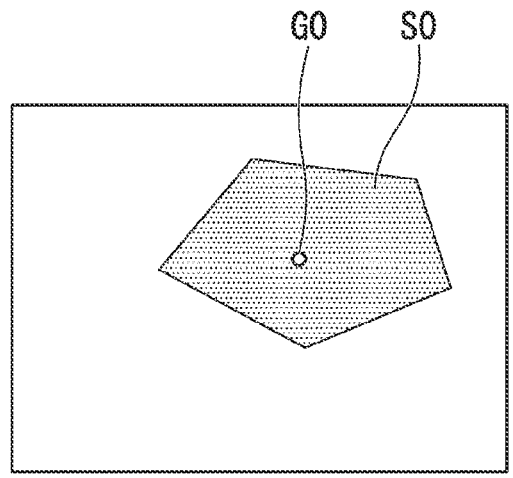
FIG. 4A is a diagram showing a projected area of a biological sample of the imaging data which is obtained by imaging the embedding block under the diffusion illumination light.
Figure 4B:
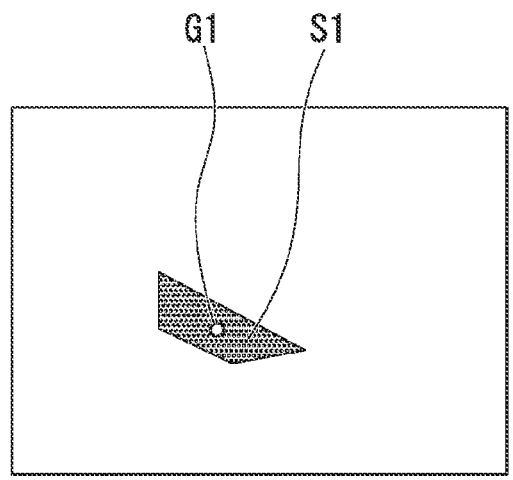
FIG. 4B is a diagram showing an exposed area of the biological sample of the imaging data which is obtained by imaging the embedding block under the epi-illumination light.

FIG. 4A shows the projected area S0 of the embedding portion of the biological sample S in the embedding block B, and FIG. 4B shows the exposed area S1 of the exposure portion of the biological sample S on the embedding block B.

For example, the projected area S0 of the embedding portion and the exposed area S1 of the exposure portion in the biological sample S can be calculated by the projected area calculation unit 41 and the exposed area calculation unit 40 based on the outline of the embedding portion and the outline of the exposure portion which are extracted as described above.

Figure 5:
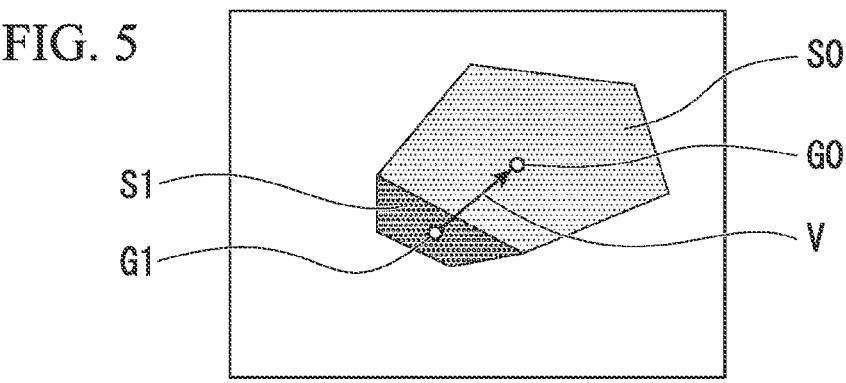
FIG. 5 is a diagram showing a vector which is directed from a center of an exposure portion of a biological sample to a center of an embedding portion thereof.
Figure 6A:
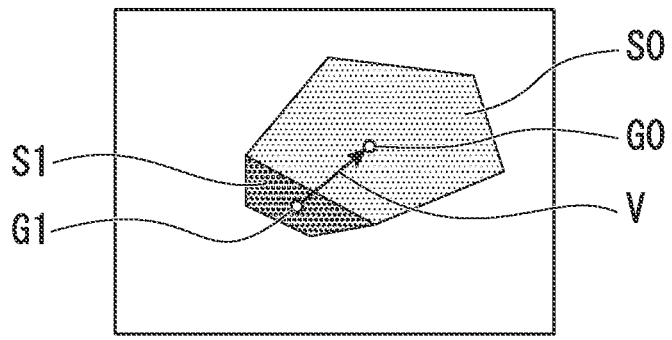
FIG. 6A is a diagram showing imaging data when an inclination angle of the embedding block is changed and cutting is performed.
Figure 6B:
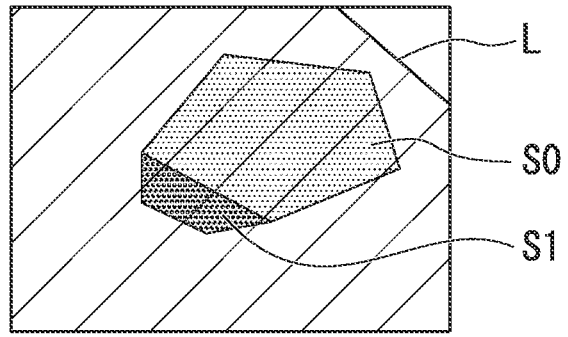
FIG. 6B is a diagram showing a change in the imaging data from FIG. 6A when the inclination angle of the embedding block is changed and the cutting is performed.
Figure 6C:
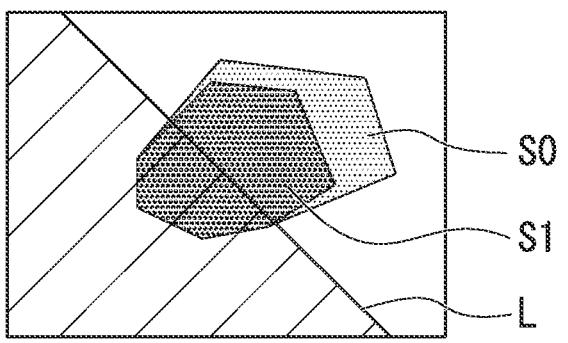
FIG. 6C is a diagram showing a further change in the imaging data when the inclination angle of the embedding block is changed and the cutting is performed.
Figure 6D:
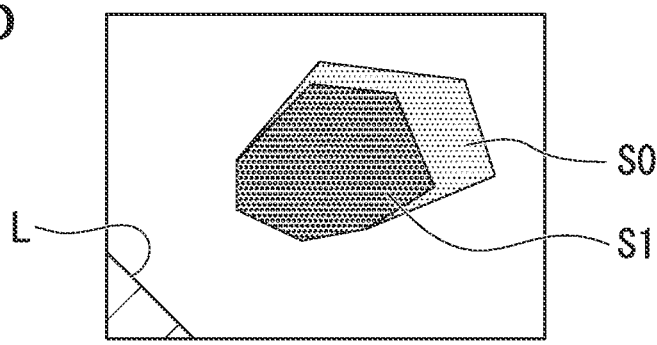
FIG. 6D is a diagram showing still a further change in the imaging data when the inclination angle of the embedding block is changed and the cutting is performed.
Figure 6E:
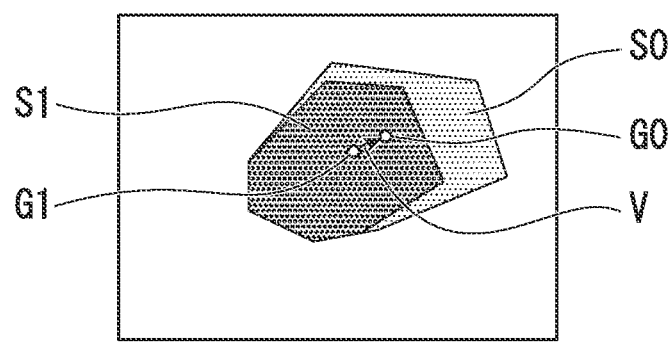
FIG. 6E is a diagram showing still a further change in the imaging data when the inclination angle of the embedding block is changed and the cutting is performed.

In FIG. 5, the images of FIGS. 4A and 4B overlap each other, and the vector V from the center G0 of the projected area S0 portion of the biological sample S in the embedding block B toward the center G1 of the exposed area S1 portion is shown. The vector V can be obtained by subtracting coordinates of the center G1 of the exposed area S1 portion from coordinates of the center G0 of the projected area S0 portion, in the vector calculation unit 42.

Moreover, when the vector V is obtained, it is not necessary that the imaging data under the epi-illumination light and the imaging data under the diffusion illumination light directly overlap each other, and processing may be performed by only numeric data.

Moreover, the control unit 45 of the general control unit 8 compares the exposed area S1 calculated by the exposed area calculation unit 40 and the projected area S0 calculated by the projected area calculation unit 41. When a ratio R (S1/S0) of the exposed area S1 with respect to the projected area S0 is larger than a first predetermined value Re (for example, 80%), that is, when the exposure state of the biological sample S reaches a desired exposure state, the operations of the moving mechanisms 12 and 15 stop (that is, the preliminary cutting of the embedding block B is completed).

In addition, during the preliminary cutting of the embedding block B, if the exposed area S1 calculated by the exposed area calculation unit 40 approaches the projected area S0 calculated by the projected area calculation unit 41, the control unit 45 controls the moving mechanism 12 of the frame portion 2 so that the amount of movement (the cutting amount by the cutting blade 3) of the support frame 10 in the Z direction is decreased according to the approaching extent.

Moreover, when the magnitude of the vector V calculated by the vector calculation unit 42 is larger than a second predetermined value (for example, 5% of an average length of sides of the embedding block B), the control unit 45 controls the rotation mechanism 11 of the frame portion 2 based on the direction of the vector V so that the absolute value of the calculated vector V is decreased (that is, so that the vector V currently calculated is cancelled). Accordingly, a relative posture of the embedding block B with respect to the cutting blade 3 is adjusted, and the preliminary cutting by the cutting blade 3 is performed.

Moreover, in FIGS. 6A to 6E, when an inclination angle of the rotation mechanism 11 of the frame portion 2 is changed and the preliminary cutting of the embedding block B is performed so that the vector V obtained by the vector calculation unit 42 approaches 0 (that is, so that cutting surface of the embedding block B is parallel to the one virtual plane H), aspects of the changes of the overlapped imaging data are sequentially shown.

As sequentially shown in FIGS. 6A to 6E, when the inclination angle of the rotation mechanism 11 is changed so that the vector V approaches 0 and the cutting of the embedding block B is advanced, if the cutting is advanced, a cutting line L moves so as to be separated from the one virtual plane H. Moreover, the inclination angles of the entire cutting surface are corrected along with the advancement of the cutting line L. As a result, compared to the FIG. 6A, the vector V is decreased in FIG. 6E.

Figure 7:
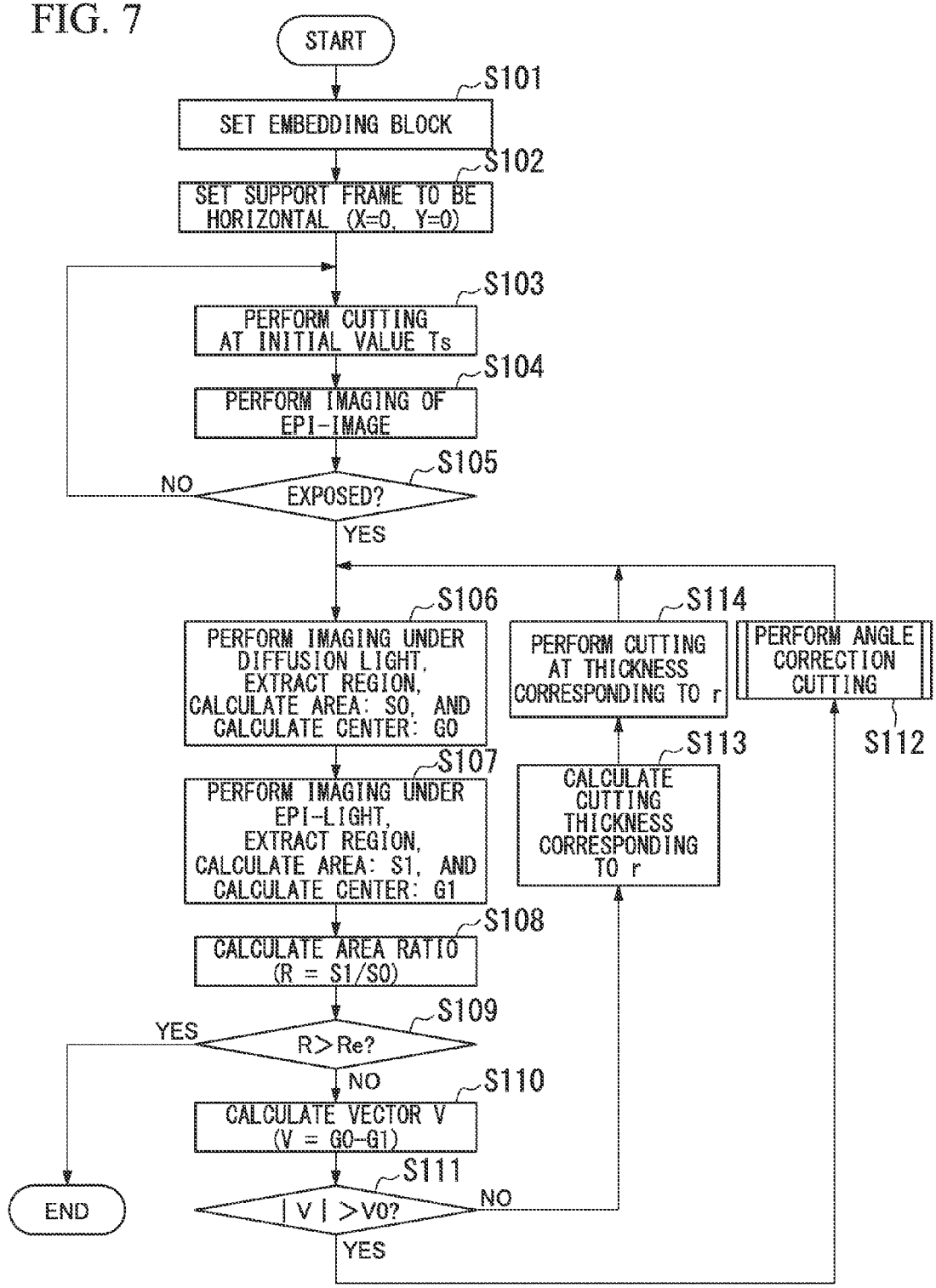
FIG. 7 is a flowchart showing a control flow in the thin section fabrication apparatus according to the embodiment of the present invention.
Figure 8:
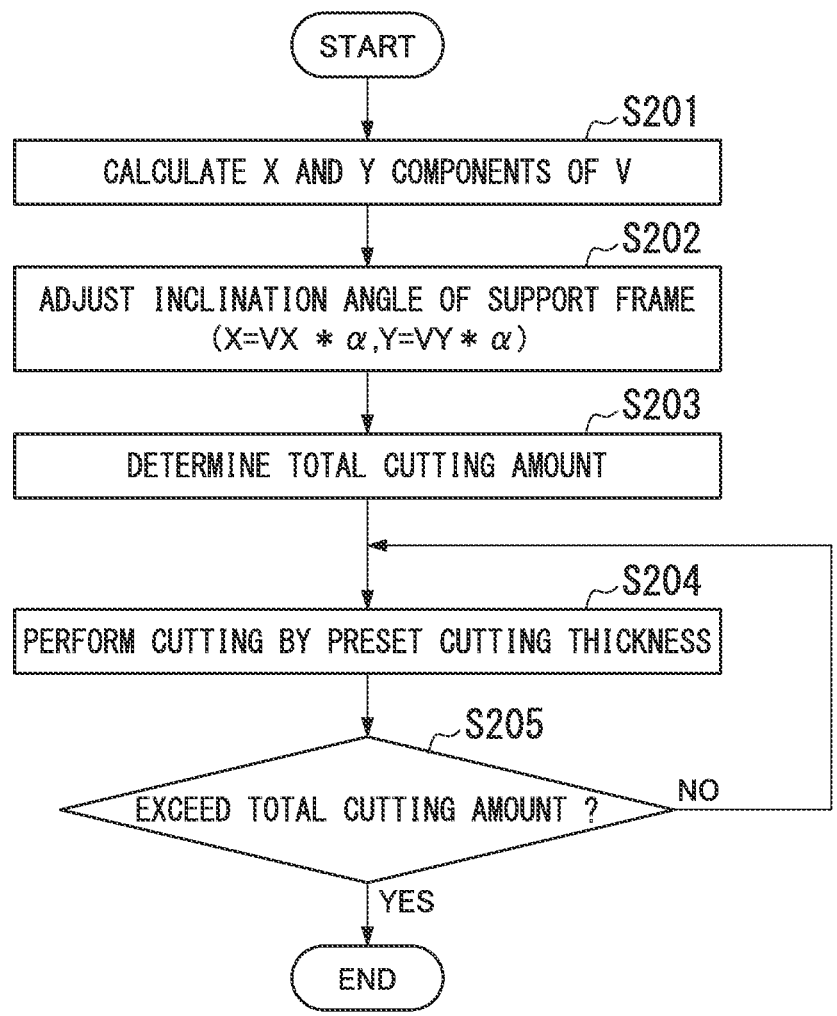
FIG. 8 is a flowchart showing a control flow in the thin section fabrication apparatus according to the embodiment of the present invention.

Next, the control by the general control unit 8 of the thin section fabrication apparatus 1 is described according to flowcharts shown in FIGS. 7 and 8.

As shown in FIG. 7, in Step S101, the embedding block B is set on the support frame 10 of the frame portion 2, and in Step S102, the rotation mechanism 11 is set to an initial state, and the support frame 10 is set to a horizontal state.

In Step S103, a one-time cutting amount (a lifting amount of the moving mechanism 12) of the embedding block B by the cutting blade 3 is set to an initial value Ts, and the preliminary cutting of the embedding block B by the cutting blade 3 starts. Moreover, the initial value Ts is appropriately set by a user.

In Step S104, the imaging of the embedding block B is performed under the epi-illumination light by the imaging unit 30, and the epi-imaging data is acquired.

In Step S105, for example, region extraction of the exposure portion of the biological sample S is performed based on the epi-imaging data, and whether or not the biological sample S is exposed to the outer surface of the embedding block B is determined according to whether or not an area of the extracted region is larger than a preset value.

In Step S105, in the case of No (when the sample is not exposed), the processing returns to Step S103 and the cutting is performed again, and at the time when it becomes Yes (when the sample is exposed), the processing proceeds to Step S106.

In Step S106, the imaging of the embedding block B is performed under the diffusion illumination light by the imaging unit 30, and after the region extraction of the embedding portion of the biological sample S is performed based on the diffusion imaging data, the projected area S0 and the center G0 of the projected area S0 portion are calculated.

In Step S107, the imaging of the embedding block B is performed under the epi-illumination light by the imaging unit 30, and after the region extraction of the exposure portion of the biological sample S is performed based on the epi-imaging data, the exposed area S1 and the center G1 of the exposed area S1 portion are calculated.

In Step S108, the ratio R (R=S1/S0) between the projected area S0 and the exposed area S1 is calculated.

In Step S109, it is determined whether or not the area ratio R is larger than the first predetermined value Re (for example, 80%) which is appropriately set by the user. In the case of Yes, the surface of the embedding block B reaches a desired exposure state, and the preliminary cutting is completed. Moreover, when the determination in Step S109 is No, the surface of the embedding block B does not reach a desired exposure state, and the processing proceeds to Step S110. Moreover, when the processing initially proceeds to Step S109, since the exposure of the biological sample S from the surface of the embedding block B is slight, the processing proceeds to Step S110.

In Step S110, the direction and the magnitude of the vector V from the center G1 of the exposed area S1 portion toward the center G0 of the projected area S0 are calculated.

In Step S111, it is determined whether or not the absolute value of the vector V obtained in Step S110 is larger than the second predetermined value V0 which is appropriately set by the user. In the case of Yes (when the absolute value is larger than the second predetermined value V0), in order to effectively cut the surface of the embedding block B to be in a desired exposure state, it is determined that the inclination posture of the embedding block B is not appropriate, and the processing proceeds to angle correction cutting process S112 described below. In the case of No (when the absolute value is less than or equal to the vector V0), it is determined that the inclination posture of the embedding block B is appropriate, and the processing proceeds to Step S113.

In Step S113, a cutting thickness t (=the lifting amount of the support frame 10) by the cutting blade 3 corresponding to the area ratio R obtained in Step S108 is calculated by a method described below.

In Step S114, the preliminary cutting by the cutting blade 3 continues according to the cutting thickness t (=the lifting amount of the support frame 10) calculated in Step S113. After Step S114, the processing returns to Step S106, and a similar loop is repeated until the area ratio R in Step S109 is larger than the first predetermined value Re.

For example, the cutting thickness t in Step S113 is calculated based on the following Equation (1).

$$t = Te + \beta \times Ts \quad (1)$$

Te: the final cutting thickness (the cutting thickness in the main cutting), $\beta$: the acceleration coefficient, and Ts: the initial value (the thickness when the preliminary cutting starts)

Moreover, Te and Ts are values which are appropriately set by the user.

Moreover, when the achievement degree of the area ratio R is defined as r (r=R/Re), according to f which is a monotone decreasing function of r, the acceleration coefficient $\beta$ can be obtained by $\beta = f(r)$. Here, in the function f(r), $\beta = 1$ is satisfied when r=0, and $\beta = 0$ is satisfied when r=1.

Therefore, the cutting thickness t calculated in Step S113 is gradually decreased as the achievement degree r (=R/Re) of the area ratio R approaches 1. At this time, of course, the amount of movement of the support frame 10 is also gradually decreased as the achievement degree r (=R/Re) of the area ratio approaches 1.

Figure 9:
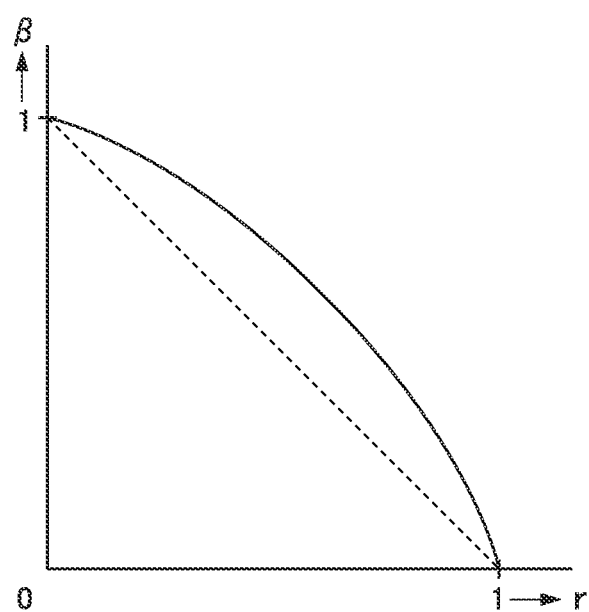
FIG. 9 is a graph showing a function $\beta=f(r)$ related to an achievement degree r of an area ratio R used in the control in the thin section fabrication apparatus according to the embodiment of the present invention.

As shown in FIG. 9, more preferably, the monotone decreasing function $\beta = f(r)$ is a function in which an arc is drawn so as to be upwardly convex according to an increase of r and the value is decreased. In this case, when the achievement degree r moves from 0 to 1, the acceleration coefficient $\beta$ approaches 0 at a faster pace than the degree r, and the cutting thickness t is rapidly decreased. Therefore, the cutting thickness can more rapidly approach the final cutting thickness Te.

FIG. 8 is a flowchart showing a flow of specific processing of the angle correction cutting process S112.

In Step S201, X and Y components (Vx, Vy) of the vector V obtained in Step S110 immediately before Step 201 are calculated.

In Step S202, the inclination angles of the X axis rotation mechanism 11b and the Y axis rotation mechanism 11a of the frame portion 2 are adjusted based on the direction of the vector V so that the vector V approaches 0. That is, in Step S202, indicated values of X=Vx×α and Y=Vy×α are output with respect to the X axis rotation mechanism 11b and the Y axis rotation mechanism 11a. Moreover, α is a coefficient which is obtained by an experiment.

In Step S203, when the inclination angle of the rotation mechanism 11 (X axis rotation mechanism 11b and Y axis rotation mechanism 11a) is adjusted in Step S202 and the preliminary cutting is performed, a total cutting amount (lifting amount of moving mechanism 12) is calculated and determined until the entire region of the surface (cutting surface) of the embedding block B is flat. The total cutting amount can be calculated from the inclination angle, the size, or the like of the embedding block B.

In Step S204, the preliminary cutting is performed on the embedding block B having the adjusted inclination angle according to the preset cutting thickness. If the preliminary cutting is progressed in this way, as shown in FIGS. 6A to 6E, the cutting line L gradually moves to a region which is separated from the region close to the cutting blade 3 at the beginning of the inclination angle adjustment.

In Step S205, it is determined whether or not the total cutting amount reaches the value determined in Step S203. In the case of Yes, the angle correction cutting process S112 ends, and in the case of No, the processing returns to Step S204, and the preliminary cutting continues.

After the angle correction cutting process S112 ends, the processing returns to Step S106 of FIG. 7, and the above-described loop is repeated until the area ratio R in Step S109 is larger than the first predetermined value Re.

As described with respect to the control flow in the above descriptions, the thin section fabrication apparatus 1 of the present embodiment adopts a method including the following processes in the preliminary cutting which is the front stage of the main cutting of the thin section.

(a) Epi-imaging Data Acquisition Process (Step S107)

A process which radiates the epi-illumination light at a right angle to the surface of the embedding block B, performs the imaging on the surface of the embedding block B in the state where the light is radiated to the surface, and acquires the epi-imaging data.

(b) Diffusion Imaging Data Acquisition Process (Step S106)

A process which radiates the diffusion illumination light to the embedding block B, performs the imaging on the surface of the embedding block B in the state where the light is radiated to the embedding block, and acquires the diffusion imaging data.

(c) Exposed Shape Extraction Process (Step S107)

A process which calculates (extracts) the exposed area (exposed shape) of the exposure portion of the biological sample S exposed to the surface of the embedding block B based on the epi-imaging data which is acquired in the epi-imaging data acquisition process.

(d) Embedded Shape Extraction Process (Step S106)

A process which calculates (extracts) the projected area (embedded shape) of the embedding portion of the biological sample S embedded in the embedding block B based on the diffusion imaging data which is acquired in the diffusion imaging data acquisition process.

(e) Preliminary Cutting Performance Process (Step S114)

A process which performs the preliminary cutting on the surface of the embedding block B by the cutting blade 3.

(f) Preliminary Cutting Ending Determination Process (Step S109)

A process which compares the exposed area (exposed shape) calculated (extracted) in the exposed shape extraction process and the projected area (embedded shape) calculated (extracted) in the embedded shape extraction process, and determines the ending of the preliminary cutting with respect to the embedding block B.

As described above, in the thin section fabrication apparatus 1 of the present embodiment, in the process of the preliminary cutting of the embedding block B, the imaging is performed (the imaging data is acquired) on the embedding block B under the epi-illumination light and under the diffusion illumination light by the imaging unit 30. The exposed area S1 and the projected area S0 of the biological sample S are calculated based on the acquired imaging data (the epi-imaging data and the diffusion imaging data), and when the ratio R of the exposed area S1 with respect to the projected area S0 is larger than the first predetermined value Re, the cutting of the embedding block B automatically stops. Therefore, a desired region having a large cross-sectional area of the biological sample S in the embedding block B can be automatically and securely exposed to the surface.

Therefore, when the thin section fabrication apparatus 1 is used, in the process of the preliminary cutting of the embedding block B, the operator does not need to perform the determination and the instruction of the cutting amount of the embedding block B each time relying on the operator's intuition, and a burden on the operator can be largely decreased.

Moreover, in the thin section fabrication apparatus 1 of the present embodiment, in the preliminary cutting of the embedding block B, the moving mechanism 12 is controlled so that the cutting amount with respect to the embedding block B is decreased as the exposed area S1 of the biological sample S on the embedding block B approaches the projected area S0 of the biological sample S in the embedding block B. Therefore, the one-time cutting amount is increased until the surface (cutting surface) of the embedding block B approaches the desired region of the biological sample S, and the embedding block B can be effectively cut. Moreover, the one-time cutting amount is gradually decreased as the surface approaches the desired region of the biological sample S, and surface roughness of the cutting surface of the embedding block B can be decreased.

Therefore, in the preliminary cutting of the embedding block B, by using the thin section fabrication apparatus 1, improvement of cutting efficiency (acceleration of operation) and smoothing of the final cutting surface of the embedding block B can be achieved.

In addition, in the thin section fabrication apparatus 1 of the present embodiment, the epi-imaging data and the diffusion imaging data of the embedding block B are acquired, and the magnitude and the direction of the vector V from the center G1 of the exposed area S1 portion toward the center G0 of the projected area S0 portion of the biological sample S are calculated based on the imaging data by the vector calculation unit 42. When the absolute value of the vector V calculated by the vector calculation unit 42 is larger than the second predetermined value V0, the rotation mechanism 11 is controlled so that the vector V approaches 0 and the preliminary cutting is performed by the cutting blade 3. Therefore, when the inclination angle of the current surface (cutting surface) of the embedding block B is largely deviated with respect to the surface passing through the desired region of the biological sample S, the angle of the embedding block B is appropriately corrected and the preliminary cutting of the embedding block B can be performed.

Therefore, by using the thin section fabrication apparatus 1, when the inclination angle of the surface of the embedding block B is largely deviated with respect to the surface passing through the desired region of the biological sample S, it is possible to effectively cut the desired region of the biological sample S at an appropriate angle.

In addition, the present invention is not limited to the above-described embodiment, and various design modifications can be performed within a scope which does not depart from the gist.

In the above-described embodiment, the area of the exposure portion and the area of the embedding portion of the biological sample are calculated based on the acquired epi-imaging data and diffusion imaging data, respectively, and the ending of the preliminary cutting is determined by comparing the calculated results. However, for example, the outline of the exposure portion and the outline of the embedding portion of the biological sample are extracted based on the acquired epi-imaging data and diffusion imaging data, and when the outlines of the extracted exposure portion and embedding portion are similar to each other or when a circumferential length difference between both is less than or equal to a predetermined value, the preliminary cutting may end.

That is, in the exposed shape extraction unit and the embedded shape extraction unit, not only are the areas of the exposure portion and the embedding portion of the biological sample calculated so as to be obtained, but characteristics of other forms such as the outline shapes or the outline lengths of the exposure portion and the embedding portion may also be extracted.

INDUSTRIAL APPLICABILITY

The present invention can be applied to a thin section fabrication apparatus and a method of fabricating a thin section which cuts an embedding block in which a biological sample is embedded and fabricates a thin section, in a preliminary stage in which a thin section sample used in physics and chemistry experiments, microscopic observation, or the like is fabricated.

DESCRIPTION OF THE REFERENCE SYMBOLS

1: thin section fabrication apparatus
2: frame portion
3: cutting blade
4: epi-illumination system (epi-imaging data acquisition unit)
5: diffusion illumination system (diffusion imaging data acquisition unit)
30: imaging unit (epi-imaging data acquisition unit and diffusion imaging data acquisition unit)
40: exposed area calculation unit (exposed shape extraction unit)
41: projected area calculation unit (embedded shape extraction unit)
42: vector calculation unit (vector calculation unit)
45: control unit (control unit)
B: embedding block
C: optical axis
P: paraffin (embedding agent)
Re: first predetermined value
S: biological sample
V: vector
V0: second predetermined value

What is claimed is:

1. A thin section fabrication apparatus, comprising:
   an epi-imaging data acquisition unit that radiates epi-illumination, performs imaging on a surface of an embedding block in which a biological sample is embedded, and acquires imaging data;
   a diffusion imaging data acquisition unit that radiates diffusion illumination, performs imaging on the surface of the embedding block, and acquires imaging data;
   an exposed shape extraction unit that extracts an exposed shape of an exposure portion of the biological sample which is exposed to a surface of the embedding block, based on the imaging data acquired by the epi-imaging data acquisition unit;
   an embedded shape extraction unit that extracts an embedded shape of an embedding portion of the biological sample which is embedded in the embedding block, based on the imaging data acquired by the diffusion imaging data acquisition unit; and
   a control unit that determines ending of the preliminary cutting by comparing the exposed shape extracted by the exposed shape extraction unit and the embedded shape extracted by the embedded shape extraction unit, and controls an operation of the preliminary cutting.

2. The thin section fabrication apparatus according to claim 1, wherein:
   the exposed shape extraction unit obtains an exposed area of the biological sample which is exposed to the surface of the embedding block, as the exposed shape;
   the embedded shape extraction unit obtains a projected area of the biological sample which is embedded in the embedding block, as the embedded shape; and
   the control unit ends the preliminary cutting when a ratio between the exposed area obtained by the exposed shape extraction unit and the projected area obtained by the embedded shape extraction unit is larger than a first predetermined value.

3. The thin section fabrication apparatus according to claim 2, further comprising:
   a vector calculation unit that obtains a center of the exposure portion of the biological sample based on the imaging data acquired by the epi-imaging data acquisition unit, obtains a center of the embedding portion of the biological sample based on the imaging data acquired by the diffusion imaging data acquisition unit, and calculates a direction and a magnitude of a vector from the center of the exposure portion toward the center of the embedding portion,
   wherein when the magnitude of the vector calculated by the vector calculation unit is larger than a second predetermined value, the control unit controls a relative posture between the embedding block and a cutting blade based on the direction of the vector so that the vector is decreased and performs the preliminary cutting.

4. The thin section fabrication apparatus according to claim 1, further comprising:
   a vector calculation unit that obtains a center of the exposure portion of the biological sample based on the imaging data acquired by the epi-imaging data acquisition unit, obtains a center of the embedding portion of the biological sample based on the imaging data acquired by the diffusion imaging data acquisition unit, and calculates a direction and a magnitude of a vector from the center of the exposure portion toward the center of the embedding portion,
   wherein when the magnitude of the vector calculated by the vector calculation unit is larger than a second predetermined value, the control unit controls a relative posture between the embedding block and a cutting blade based on the direction of the vector so that the vector is decreased and performs the preliminary cutting.

5. The thin section fabrication apparatus according to claim 1,
   wherein the control unit performs the preliminary cutting so that a cutting amount of the preliminary cutting is decreased as the exposed shape extracted by the exposed shape extraction unit approaches the embedded shape extracted by the embedded shape extraction unit.

6. The thin section fabrication apparatus according to claim 1, further comprising:
   a cutting blade that performs the preliminary cutting on the surface of the embedding block and causes the biological sample to be in a desired exposure state.

7. A method of fabricating a thin section, in which after preliminary cutting is performed on a surface of an embedding block, in which a biological sample is embedded, by a cutting blade so as to cause the biological sample to be in a desired exposure state, main cutting is performed on the embedding block to cut out a thin section, comprising:
   an epi-imaging data acquisition process of performing imaging on the surface of the embedding block by radiating epi-illumination to acquire imaging data;
   a diffusion imaging data acquisition process of performing imaging on the surface of the embedding block by radiating diffusion illumination to acquire imaging data;
   an exposed shape extraction process of extracting an exposed shape of an exposure portion of the biological sample which is exposed to a surface of the embedding block, based on the imaging data acquired in the epi-imaging data acquisition process;
   an embedded shape extraction process of extracting an embedded shape of an embedding portion of the biological sample which is embedded in the embedding block, based on the imaging data acquired in the diffusion imaging data acquisition process;
   a preliminary cutting performance process of performing preliminary cutting on the surface of the embedding block by a cutting blade; and
   a preliminary cutting ending determination process of determining ending of the preliminary cutting by comparing the exposed shape extracted in the exposed shape extraction process and the embedded shape extracted in the embedded shape extraction process.

* * * * *